United States Patent
Dippl et al.

(10) Patent No.: US 7,144,157 B2
(45) Date of Patent: Dec. 5, 2006

(54) DRAWER FOR X-RAY DETECTORS

(75) Inventors: Thomas Dippl, Pressath (DE); Peter Rauh, Schnabelwaid (DE); Claus-Günter Schliermann, Kemnath (DE); Dieter Wöhrl, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/996,886

(22) Filed: Nov. 24, 2004

(65) Prior Publication Data

US 2005/0135564 A1 Jun. 23, 2005

Related U.S. Application Data

(60) Provisional application No. 60/525,706, filed on Nov. 28, 2003.

(30) Foreign Application Priority Data

Nov. 28, 2003 (DE) ................ 103 56 289

(51) Int. Cl.
*G03B 42/02* (2006.01)
(52) U.S. Cl. .................. 378/177; 378/167; 378/181
(58) Field of Classification Search ............. 378/167, 378/177, 181, 189
See application file for complete search history.

(56) References Cited

U.S. PATENT DOCUMENTS 3,920,997 A * 11/1975 Munch .................. 378/167
4,232,227 A * 11/1980 Finkenzeller et al. ....... 378/177
5,465,285 A * 11/1995 Gall et al. ............... 378/173

FOREIGN PATENT DOCUMENTS

| DE | 29 11 911 A1 | 10/1979 |
|---|---|---|
| DE | 30 34 282 A1 | 9/1980 |
| DE | 285 846 A5 | 1/1991 |
| EP | 0 218 594 B1 | 2/1986 |
| WO | WO 0133921 A1 | 5/2001 |

OTHER PUBLICATIONS

Siemens, UROSKOP® D "A class of its own in urology" 1996.
Translation of German Office Action, dated Jan. 26, 2006 on DE 103 56 289.3-54, Siemens 2003P12752DE.
German Office Action dated Jan. 26, 2006.

* cited by examiner

*Primary Examiner*—Edward J. Glick
*Assistant Examiner*—Chih-Cheng Glen Kao
(74) *Attorney, Agent, or Firm*—Brinks, Hofer, Gilson & Lione

(57) ABSTRACT

A detector drawer for an X-ray detector has at least one stop (5) by which the mobility of an inserted X-ray detector in at least one direction is restricted. The mobility of the inserted X-ray detector is hindered by the at least one stop to two alternate stop positions with respect to that direction; and that the respective stop position becomes operative as a function of the motion of the X-ray detector upon its insertion, for instance as a function of the direction of the motion. By using the alternate stop positions, which automatically become operative, portable digital X-ray detectors, which are constructed asymmetrically, are automatically positioned centrally in the detector drawer regardless of their orientation or the desired orientation of the image to be made. The detector drawer is advantageously used in an X-ray system, and desirably in an X-ray system with a detector that is pulled out from opposite sides of a patient examination table.

14 Claims, 3 Drawing Sheets

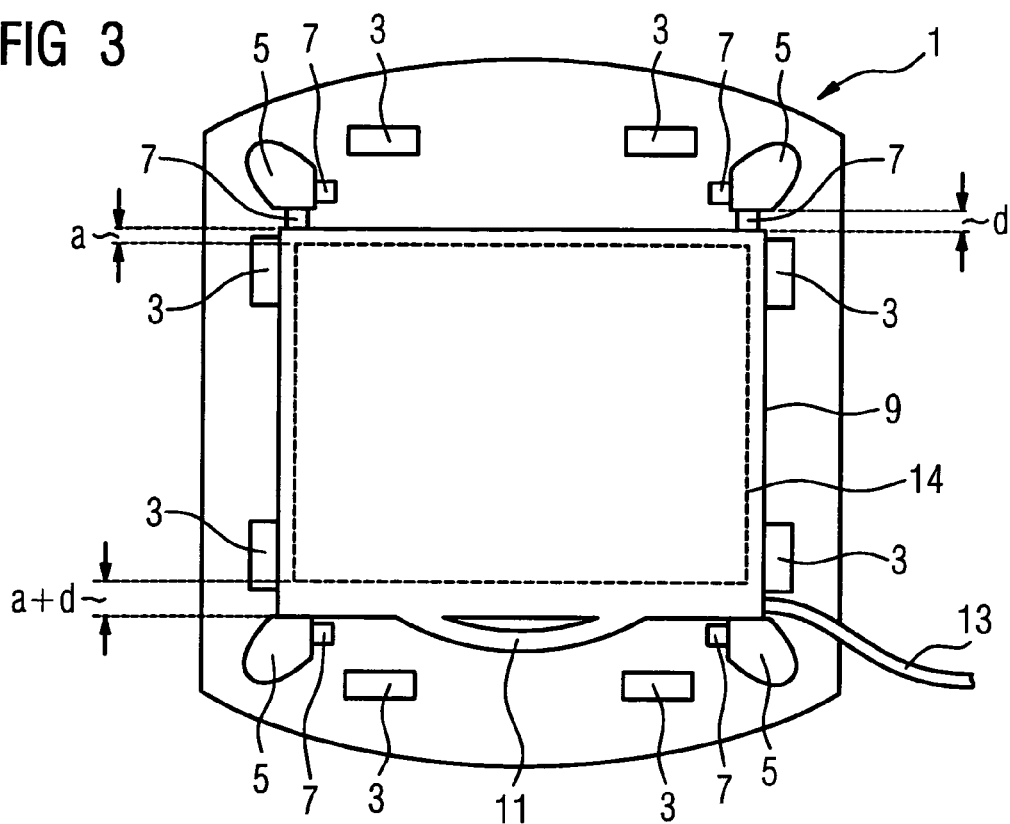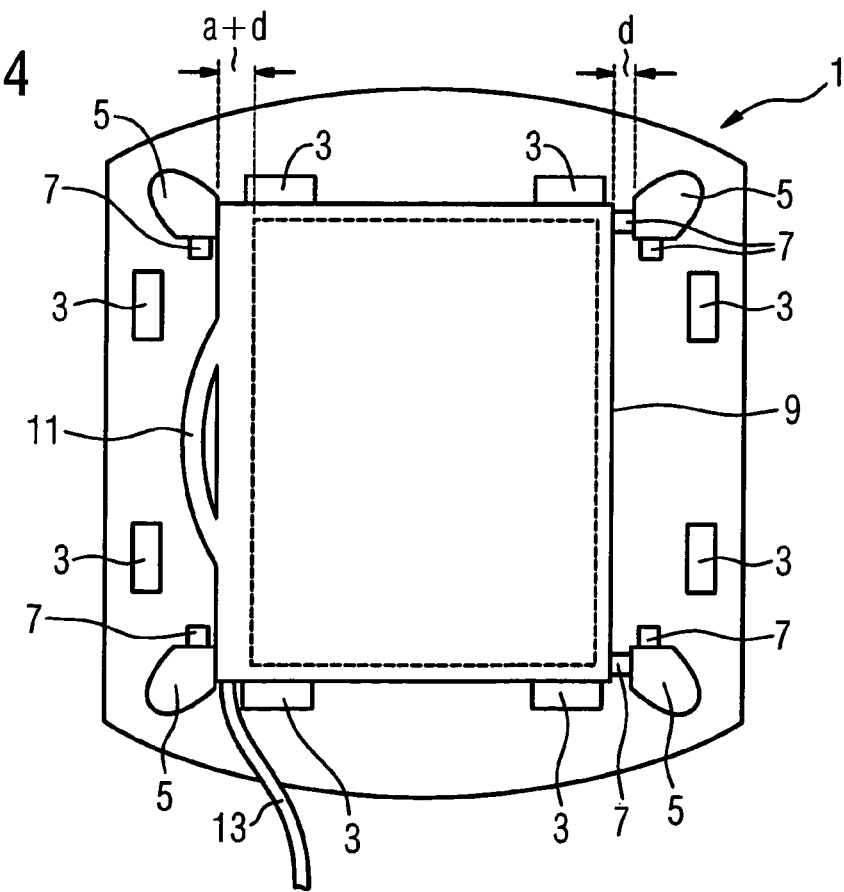

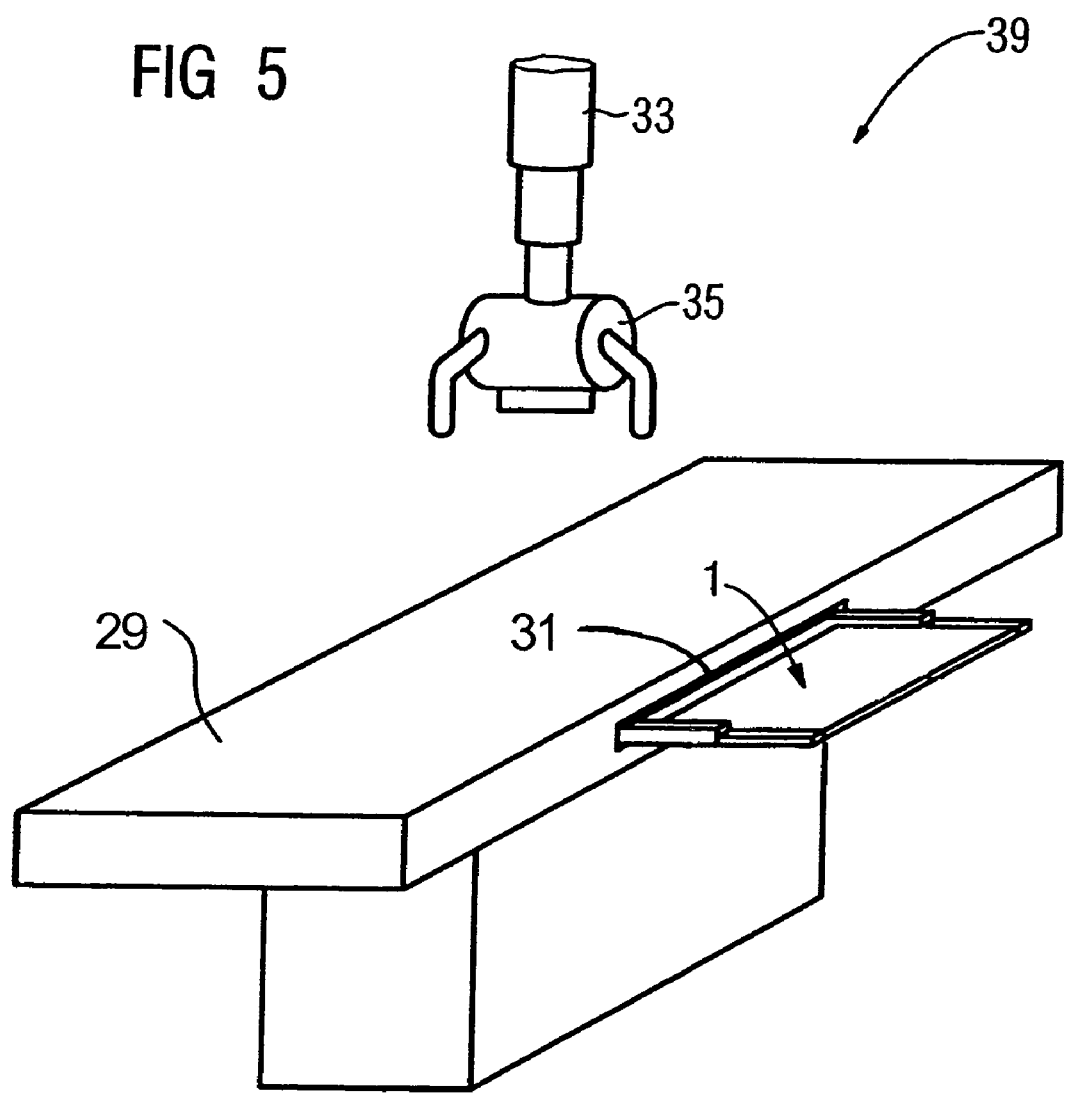

DRAWER FOR X-RAY DETECTORS

REFERENCE TO RELATED APPLICATIONS

The present patent document claims the benefit of the filing date under 35 U.S.C. §119(e) of provisional U.S. patent application Ser. No. 60/525,706, filed Nov. 28, 2003, which is hereby incorporated by reference.

BACKGROUND

The invention relates, in general, to X-ray detectors, and more particularly, to a detector drawer for an X-ray detector, in which a mobility or advancement of the inserted X-ray detector in at least one direction is restricted.

Detector drawers for inserting X-ray detectors are used in X-ray examination equipment, or X-ray systems. X-ray systems have an X-ray source for generating X-rays that pass through a patient body to be examined radiologically and are then detected by an X-ray detector. The X-ray detector, either a conventional sheet film system or a digital detector, is positioned in the X-ray beam generated by the X-ray source. The positioning is done via a detector drawer into which the X-ray detector is placed and which is inserted, with the detector in place, into a receptacle of the X-ray system.

In Bucky systems, for example, the patient to be examined is positioned on a patient examination or supporting table and X-rays originating from an X-ray source disposed above the table pass through him. The receptacle for the detector drawer can be pulled out like a drawer so that the X-ray detector can be placed therein and is then pushed in again. The X-ray detector is thus positioned underneath the patient.

Currently available Bucky systems are usually still configured for analog X-ray detectors on the basis of sheet film systems, since digital X-ray detectors have only been available quite recently. From International Patent Disclosure WO 01/33921, it is disclosed that to convert a Bucky system designed for analog detectors into a digital system, a digital X-ray detector may be inserted into the receptacle of the patient examination table instead of the analog X-ray film cassette. As such, the detector is installed in an adaptively configured detector drawer. Both the detector drawer and the X-ray detector are adapted to one another. To make different picture-taking formats possible, such as landscape and portrait, the detector can be rotated in the detector drawer.

Desirably, one may want to use a commercially available portable digital X-ray detector that does not have to be a priori adapted to the detector drawer. Such detectors have an electric cable connection for supplying power and for transmitting the detector signals. The electrical cable should be taken into account when the detector is inserted into the detector drawer; the cable should not become kinked nor sheared off. The electrical cable can, therefore, be guided only in such a way as to extend out of the receptacle opening in the patient examination table. From there, the electrical cable may extend to a control unit for the X-ray system. Such trailing cable may present a potential risk of stumbling and be a hindrance to medical personnel walking up to or moving around the patient examination table. Depending on the intended examination, however, the capability of approaching the patient from all sides may be desirable.

In order to reach the patient from either side of the patient examination table to suit a given situation and to minimize encountering problems in manipulating the detector drawer, a patient examination table with a receptacle open on two sides for the insertion of the drawer is known from the X-ray system known as Uroskop D, made by Siemens A G. A system with a receptacle open on two sides is also disclosed in German Patent Disclosure DE 30 34 282. A detector drawer can be inserted from both opposite sides of the examination table into the receptacle open on those two sides. If a portable digital X-ray detector is used, the receptacle open on two sides may be used in such a way that the detector is inserted from one side of the examination table from which medical personnel do not have to approach the patient. One can thus be assured that the cable does not have to be in the way of the medical personnel.

Because of an asymmetrical outline of portable X-ray detectors, in which an actual detection field is not centered, substantially exact positioning of the detector in the X-ray beam may not be assured. Further, depending on an insertion direction or an associated orientation of the detector, the positioning may change.

OBJECT AND SUMMARY

The present invention is defined by the following claims. This description summarizes some aspects of the present embodiments and should not be used to limit the claims.

One object is to provide a detector drawer into which an X-ray detector of asymmetrical outline, such as a portable X-ray detector, can be inserted with alternate orientations without resulting in alternate positioning of the detection field in the X-ray beam.

Another concept is to provide a detector drawer for an X-ray detector, which drawer has at least one stop by which a mobility of an inserted X-ray detector in at least one direction is restricted. In such detector drawer, the mobility of the inserted X-ray detector can be arrested by a stop at two alternate stop positions with respect to the restricted direction, and the respective stop position becomes operative as a function of the motion of the X-ray detector upon insertion.

Since X-ray detectors are normally inserted from a front side of the detector drawer, alternate motions of the X-ray detector may occur as by-products of the insertion process such as upon an approach to a stop on the front side and to a stop on a back side of the detector drawer. After the X-ray detector is thrust against the stop toward the back side in the insertion direction and has reached the rear stops, the X-ray detector is lowered on its front end onto the front side stops.

Because of the different directions of motion or advancement, different stop positions for the back and front stops may also occur on their own. Because of the resulting different stop positions, the nonsymmetrical outline of a digital detector, such as a flat detector (FD), can automatically be compensated in such a way that a positioning of the detection field centrally in the X-ray beam is automatically established. The automatically adjustable positioning stops may allow relatively simple manipulations of the X-ray detector, since stops and guides that are typically manually reinserted or adjusted can be dispensed with. Instead, one and the same detector drawer may be used automatically for an X-ray detector to be inserted with arbitrary orientations.

In an advantageous feature, the respective stop position becomes operative as a function of whether the X-ray detector is moved in the aforementioned direction or in a direction perpendicular toward the stop. As a result, the alternate stop positions become operative as a function of different directions of motion of the X-ray detector, which assures a substantial protection against error in the operation of the automatically adjustable stops. Moreover, in the aforementioned course of motion upon insertion of the detector into a detector drawer, in which the detector is first thrust against the stops located at a distance and is then lowered onto the closer stops, motions oriented perpendicular to one another also occur in practical use. That is, the directions of motion that occur in the typical course of motion may be utilized for automatically adjusting the stop position, which simplifies the process of positioning the X-ray detector.

In a further advantageous feature, the stop has a pivot lever, which is pivotable about a shaft parallel to the detector drawer. Such pivot lever may represent a substantially simple structural way of repositioning a stop. Upon motions counter to the pivot lever and parallel to the detector drawer, the stop predetermines a first stop position, and, upon motions in a direction perpendicular, the stop swivels out of the way downward, for instance, and predetermines a second stop position. Upon motions in a direction perpendicular, the stop swivels out of the way downward, for instance, and predetermines a second stop position Illustrative and exemplary embodiments of the invention are described in further detail below with reference to and in conjunction with the figures.

BRIEF DESCRIPTION OF THE DRAWINGS

FIG. 3 is a schematic plan view of the detector drawer of FIG. 1 with adjustable stops and an X-ray detector inserted;

FIG. 4 is schematic plan view of the detector drawer of FIG. 1 with an X-ray detector inserted with a different orientation; and FIG. 5 illustrates schematically an X-ray system.

DETAILED DESCRIPTION OF THE DRAWINGS

Figure 1:
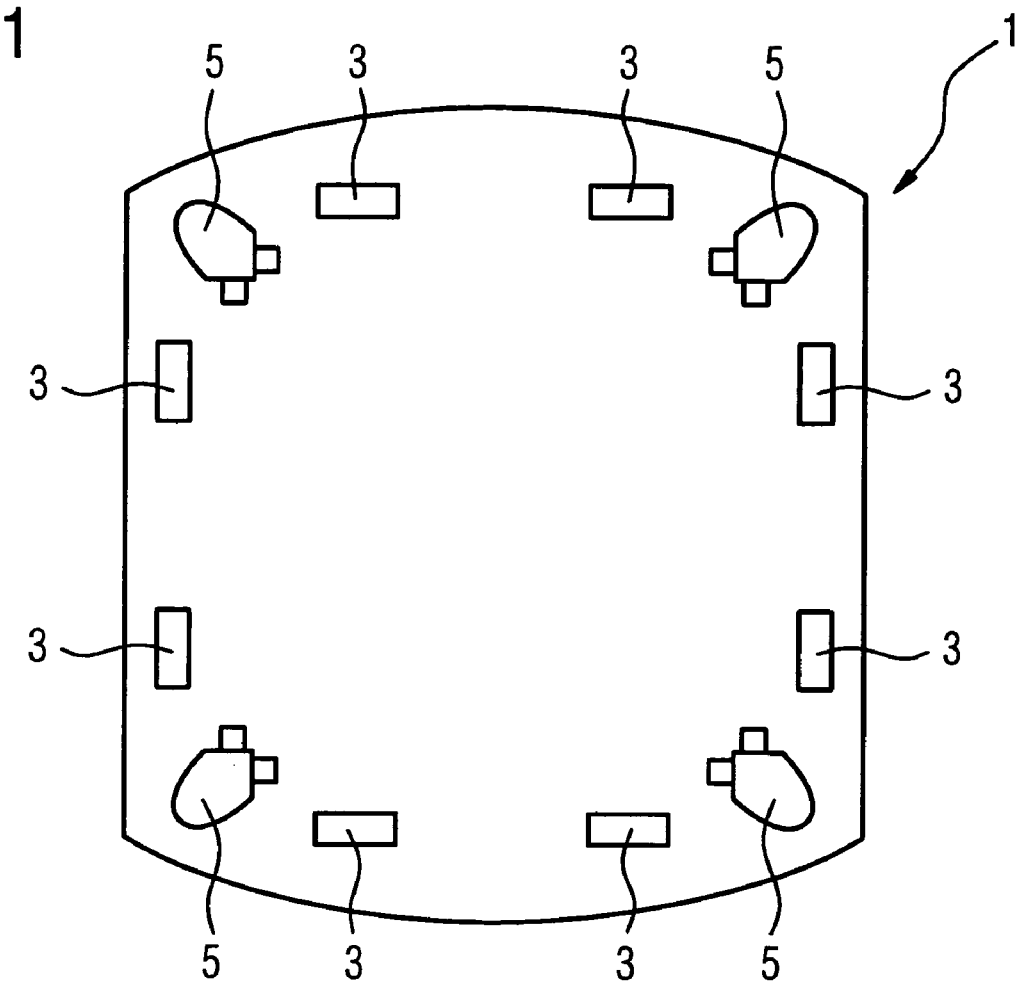
FIG. 1 is a schematic plan view of a detector drawer with variable stops.

In FIG. 1, a detector drawer 1 is shown schematically in plan view. The detector drawer 1 has two parallel, rectilinear edges in the insertion direction. On the other two opposed edges, handles, for instance, for pushing the drawer in and pulling it out can be provided, but are not shown in the drawing.

The detector drawer 1 has guides 3, which serve to guide an X-ray detector during an insertion into the detector drawer 1. For instance, a substantially rectangular X-ray detector may be guided between two opposed guides 3 in such a way that a lateral motion is prevented by the guides 3, and a longitudinal motion is enabled.

Furthermore, individual stops 5 are provided in all four corners of the detector drawer 1. With respect to the transverse and longitudinal extent of the detector drawer, the stops 5 are each disposed symmetrically in pairs opposite one another and serve to limit the motion of an X-ray detector to be inserted by causing the X-ray detector to strike one or more of the stops 5. The stops 5 are fixedly mounted on the detector drawer 1, but the stops 5 each have two different stop positions in each of the two respective possible stop directions. These stop positions occur automatically as a function of the motion of the X-ray detector upon striking or making contact with the respective stop 5.

Figure 2:
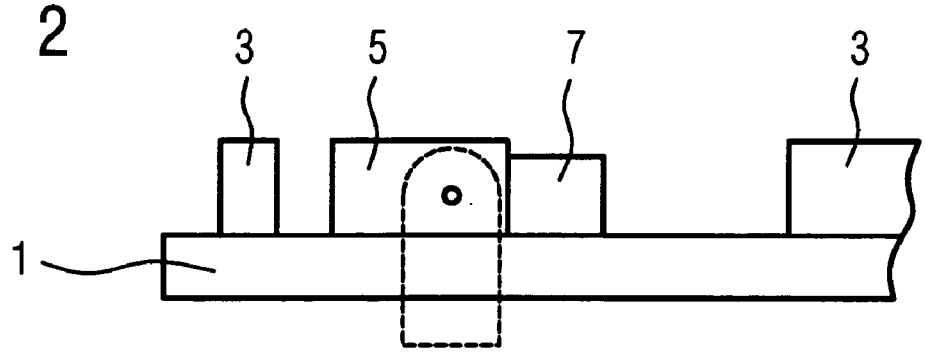
FIG. 2 is a schematic side view of a pivot lever stop.

In FIG. 2, operatively adjustable stops 5 that are relatively simple to realize are shown. FIG. 2 shows a portion of the detector drawer 1 in a side view. As described in the preceding discussion of FIG. 1, guides 3 and a stop 5 are shown on the detector drawer 1.

The stop 5 has two alternate stop positions, which become operative as a function of the motion of the x-ray detector upon approaching the stop 5. These alternate stop positions are realized via a pivot lever 7, which is supported pivotably about a shaft parallel to the detector drawer 1. From an original position, the pivot lever 7 may assume an orientation parallel to the detector drawer 1, which is represented in the drawing by a solid line. In this orientation, the detector drawer may be held elastically but firmly, for instance by a spring force. However, the detector drawer may also assume a further position, one that is oriented perpendicular to the detector drawer 1, which is shown in dashed lines in the drawing. To assume this orientation, the pivot lever 7 pivots out of the original position downward into a corresponding opening or indentation in the detector drawer 1.

Because of the shape of the pivot lever 7 and its pivotable support, the pivot lever 7 may enable two alternate stop positions that become operative automatically. If an X-ray detector is thrust against the pivot lever 7 parallel to the detector drawer 1, in other words from the right relatively to FIG. 2, the pivot lever does not move away downward. Accordingly, the pivot lever 7 predetermines a first stop position. If however the same or a similar X-ray detector approaches the pivot lever 7 from a direction perpendicular to the detector drawer 1 in other words from above relatively to FIG. 2, then the pivot lever does pivot downward and away. As such, the stop 5 becomes operative as a stop and predetermines a second stop position. In the drawing of FIG. 2, this second stop position is located to the left of the first stop position that is formed by the pivot lever 7.

In FIG. 3, the detector drawer 1 of FIGS. 1 and 2 is shown in a plan view, but with the X-ray detector 9 inserted. As described above, the detector drawer 1 has guides 3 and operatively adjustable stops 5 with pivot levers 7. The X-ray detector has a substantially rectangular outline.

The X-ray detector 9 inserted into the detector drawer 1 is a portable digital X-ray detector. The portable detector has a handle 11, by which it can be grasped and carried. The X-ray portable detector also has an electrical cable 13, through which power supply and signal transmission lines extend. Inside the detector 9, the power supply and signal transmission lines are not shown in detail as well as an associated set of detector electronics. Because of these electronics, the detection field 14 is not disposed entirely symmetrically and is therefore not located entirely centrally inside the X-ray detector 9. The outline of the detection field 14 is represented by dashed lines and is rectangular, so that by rotating the X-ray detector by 90°, a change can be made between two imaging formats, namely upright (portrait) and crosswise (landscape). The detection field 14 is spaced apart from the handle 11 by the distance marked d, and instead of detector elements, parts of the electronics and the connection for the cable 13 are on a side toward the handle 11.

As shown in FIG. 3, the X-ray detector 9 may not rest in a centered fashion on the detector drawer 1. Instead, the X-ray detector position may be displaced in the direction of the handle 11. This displacement is dimensioned such that the asymmetrical inner construction of the X-ray detector 9 is compensated; and the detection field 14, not disposed centered in the detector, is disposed centrally relative to the detector drawer 1. This displacement is marked d in the drawing and corresponds to the displacement of the detection field 14 inside the X-ray detector 9.

The non-central positioning of the X-ray detector 9 is engendered by the alternate stop positions of the adjustable stops 5. As viewed from the handle 11, the detector is guided laterally by the guides 3. A side edge of the detector 9 opposite the handle 11 strikes the pivot levers 7 of the stops 5 in their alternate stop positions. Thus, the two associated stops 5 adjust the motion of this detector side edge in the first of two alternate stop positions.

Conversely, the pivot levers 7 of the two stops 5 disposed toward the handle are swiveled out of the way, so that the stop faces of the stops 5 themselves determine the stop position. Thus the motion of the X-ray detector 9 in this direction is restricted by the second stop position of each of the adjustable stops 5.

The alternate stop positions differ by the same spacing d by which the detection field 14 is displaced inside the X-ray detector 9. Thus the pivot levers 7 likewise have the dimension d shown in the drawing.

The alternate stop positions become operative automatically by the motion of the X-ray detector 9 upon insertion into the detector drawer 1. To insert the X-ray detector 9, the operator or user of the system grasps the X-ray detector 9 by the handle 11 and places the X-ray detector 9 with the handle opposite edge situated between the guides 3 on the detector drawer 1. Thus guided, the X-ray detector 9 is thrust away from the handle side to abut against the stops 5 located at a distance. As such, in a motion parallel to the detector drawer 1, the X-ray detector 9 may strike the pivot levers 7, which as described above do not swivel out of the way upon this motion. In this way, the stop position is automatically predetermined by the pivot levers 7.

Once thrust with the aid of the handle 11 against the distal stops 5 located at a distance, the X-ray detector 9 is lowered on the handle end onto the correspondingly near stops 5. In the process, arriving from above, that is, perpendicular to the detector drawer 1, the X-ray detector 9 strikes the pivot levers 7, which in the process swivel downward, out of the way. The stop position is therefore formed not by the pivot levers 7 but rather by the stop faces of the near stops 5, which is why the second of the two alternate stop positions becomes operative automatically.

In FIG. 4, the same detector drawer 1 as in the FIG. 3 drawing described above is shown, again with the X-ray detector 9 inserted. However, the X-ray detector 9 is inserted with an orientation rotated 90° clockwise. In accordance with this rotation, the positioning of the detection field 14 located inside the detector is also different. The detection field 14 is represented by dashed lines in the drawing and is displaced to the right by the distance d. Conversely, in the FIG. 3 drawing, the detection field 14 is displaced upward by the distance d. So that the detection field may be positioned in the center of the detector drawer 1 despite the changed orientation, the stops 5 become operative in alternate stop positions than in the FIG. 3 drawing. While in FIG. 4, the distal stops 5 shown at the top each become operative in the first stop position, and the near stops 5 shown at the bottom each become operative in the second stop position, in FIG. 5 the stops 5 shown on the right become operative in the first stop position, and the stops shown on the left become operative in the second stop position.

The change in the operative stop positions arises automatically from the rotation of the X-ray detector 9, if—as described in the preceding FIG. 3 drawing—the X-ray detector 9 has been inserted, namely as a result of placement of the edge away from the handle 11 and pushing this edge as far as the respective stops 5 and subsequent lowering of the edge toward the handle of the detector 9. Comparing the preceding drawing, FIG. 3, with FIG. 4 substantially clarifies how, via the operatively adjustable stops 5, a central orientation of the detector elements of the portable X-ray detector 9 is assured automatically, regardless of its orientation, without having to make manual changes to the stops 5 or the detector drawer 1 or the X-ray detector 9.

In FIG. 5, an X-ray system or so-called Bucky system 39 is shown schematically. An X-ray source 35 is secured to a ceiling mount 33. The X-ray source 35 serves to generate an X-ray beam, which in the drawing extends with a downward orientation. Below the X-ray source 35 is a patient examination or supporting table 29, on which a patient to be examined may for instance be located or positioned. The patient examination table 29 has a receptacle 31, into which a detector drawer 1 can be inserted. If an X-ray detector is located in the detector drawer 1, then the X-radiation originating from the X-ray source 35 may pass through a patient located above the receptacle 31, and the X-radiation can then be detected by the X-ray detector located in the receptacle 31.

Although not visible from the FIG. 5 drawing, the receptacle 31 is open on two sides, so that a detector drawer 1 may be inserted from both opposite sides of the patient examination table 29. The detector drawer 1 and the receptacle 31 may have a slide-through stop, which may not allow the detector drawer 1 from being thrust all the way through the receptacle 31 if an X-ray detector is in place therein. Via the slide-through stop, the above-described detector drawer 1 may be used with a portable digital X-ray detector. As such, the X-ray detector may be inserted from both sides of the examination table. Further, independently of the insertion side, the digital X-ray detector may be inserted as far as the central stop in the receptacle 31 without the detector drawer being thrust all the way through the receptacle 31 and the detector cable sheared off or torn off in the process.

The invention claimed is:

1. A detector drawer for an X-ray detector, the detector drawer comprising:
    at least one stop by which an advancement of an inserted X-ray detector in at least one direction is restricted,
    wherein the advancement of the inserted X-ray detector is restricted by the at least one stop to two alternate stop positions with respect to the at least one direction, and wherein a respective stop position becomes operative as a function of the advancement of the X-ray detector during insertion.

2. The detector drawer of claim 1, wherein the respective stop position becomes operative as a function of whether the X-ray detector is advanced in the at least one direction or in a direction perpendicular to the at least one direction to abut against the stop.

3. The detector drawer of claim 2, wherein the at least one stop has a pivot lever, which is pivotable about a shaft parallel to the detector drawer.

4. The detector drawer of claim 3, wherein the at least one stop comprises a plurality of stops disposed symmetrically with respect to a length and a width of the detector drawer.

5. The detector drawer of claim 2, wherein the at least one stop comprises a plurality of stops disposed symmetrically with respect to a length and a width of the detector drawer.

6. The detector drawer of claim 1, wherein the at least one stop comprises a plurality of stops disposed symmetrically with respect to a length and a width of the detector drawer.

7. A patient examination table for an X-ray system, the patient examination table comprising:
    a receptacle into which a detector drawer is insertable, the detector drawer configured for an X-ray detector and having at least one stop by which an advancement of an inserted X-ray detector in at least one direction is restricted, and wherein the advancement of the inserted X- ray detector is restricted by the at least one stop to two alternate stop positions with respect to the at least one direction, and wherein a respective stop position becomes operative as a function of the advancement of the X-ray detector during insertion.

8. The patient examination table of claim 7, wherein the respective stop position becomes operative as a function of whether the X-ray detector is advanced in the at least one direction or in a direction perpendicular to the at least one direction to abut against the stop.

9. The patient examination table of claim 8, wherein the at least one stop has a pivot lever which is pivotable about a shaft parallel to the detector drawer.

10. The patient examination table 9, wherein the at least one stop comprises a plurality of stops disposed symmetrically with respect to a length and a width of the detector drawer.

11. The patient examination table of claim 7, wherein the receptacle has an opening on each of two opposed sides of the patient examination table, and wherein the detector drawer is configured to be inserted into the receptacle from either side.

12. An X-ray system comprising:

a patient examination table which has a receptacle into which a detector drawer is insertable, the detector drawer adaptively configured for an X-ray detector and having at least one stop by which an advancement of an inserted X-ray detector in at least one direction is restricted, and wherein the advancement of the inserted X- ray detector is restricted by the at least one stop to two alternate stop positions with respect to the at least one direction, and wherein a respective stop position becomes operative as a function of the advancement of the X-ray detector during insertion.

13. The X-ray system of claim 12, wherein the receptacle has an opening on each of two opposed sides of the patient examination table, and wherein the detector drawer is configured to be inserted into the receptacle from either side.

14. The X-ray system of claim 12 further comprising an X-ray source positioned above the patient examination table.

* * * * *